(12) United States Patent
Yamada

(10) Patent No.: US 9,528,978 B2
(45) Date of Patent: Dec. 27, 2016

(54) BLOOD ANALYZER AND BLOOD ANALYZING METHOD

(71) Applicant: Sysmex Corporation, Kobe-shi, Hyogo (JP)

(72) Inventor: Kazuhiro Yamada, Kobe (JP)

(73) Assignee: Sysmex Corporation (JP)

( * ) Notice: Subject to any disclaimer, the term of this patent is extended or adjusted under 35 U.S.C. 154(b) by 0 days.

(21) Appl. No.: 14/862,616

(22) Filed: Sep. 23, 2015

(65) Prior Publication Data

US 2016/0091484 A1   Mar. 31, 2016

(30) Foreign Application Priority Data

Sep. 26, 2014   (JP) .................. 2014-196279

(51) Int. Cl.
*G01N 33/48*   (2006.01)
*G01N 33/49*   (2006.01)
(Continued)

(52) U.S. Cl.
CPC ....... *G01N 33/4915* (2013.01); *G01N 15/0211* (2013.01); *G01N 15/1436* (2013.01);
(Continued)

(58) Field of Classification Search
CPC ............ G01N 21/3151; G01N 15/1484; G01N 2015/1486; G01N 21/31; G01N 21/8483; G01N 15/147; G01N 15/1434; G01N 15/1404; G01N 2015/0073; G01N 2015/008; G01N 2015/1075; G01N 15/1459; G01N 15/1475
See application file for complete search history.

(56) References Cited

U.S. PATENT DOCUMENTS 4,983,359 A * 1/1991 Tomioka ............ G01N 15/1459
356/39
5,427,920 A * 6/1995 Berndt ................. G01N 21/253
356/339
(Continued)

FOREIGN PATENT DOCUMENTS

EP   2 293 062 A1   3/2011
EP   2 784 480 A2   10/2014
(Continued)

OTHER PUBLICATIONS

Neukammer, V. et al., "Flow Cytometric Differentiation of Erythrocytes and Leukocytes in Dilute Whole Blood by Light Scattering", *Cytometry*, vol. 32, No. 3, Jul. 1, 1998, pp. 191-197.
(Continued)

*Primary Examiner* — Michael P Stafira
(74) *Attorney, Agent, or Firm* — Brinks Gilson & Lione

(57) ABSTRACT

A blood analyzer comprises a flow cell, a first light source, a second light source, a first light receiving part, a second light receiving part, and a processing unit. The processing unit obtains values related to the number of red blood cells, the number of white blood cells, and hemoglobin based on a first scattered light information based on the signals output from the first light receiving part, and a second scattered light information based on the signals output from the second light receiving part.

18 Claims, 14 Drawing Sheets

(51) Int. Cl.
*G01N 15/02* (2006.01)
*G01N 33/50* (2006.01)
*G01N 35/00* (2006.01)
*G01N 21/05* (2006.01)
*G01N 21/51* (2006.01)
*G01N 21/53* (2006.01)
*G01N 15/14* (2006.01)
*G01N 15/00* (2006.01)
*G01N 21/64* (2006.01)

(52) U.S. Cl.
CPC ......... *G01N 15/1459* (2013.01); *G01N 21/05* (2013.01); *G01N 21/51* (2013.01); *G01N 21/53* (2013.01); *G01N 21/532* (2013.01); *G01N 33/5094* (2013.01); *G01N 35/00871* (2013.01); *G01N 2015/008* (2013.01); *G01N 2015/0073* (2013.01); *G01N 2015/0084* (2013.01); *G01N 2015/1438* (2013.01); *G01N 2015/1486* (2013.01); *G01N 2021/6419* (2013.01); *G01N 2021/6421* (2013.01); *G01N 2035/00891* (2013.01)

(56) References Cited

U.S. PATENT DOCUMENTS

| | | | | |
|---|---|---|---|---|
| 5,817,025 | A | * | 10/1998 | Alekseev ............ G01J 3/4412 356/339 |
| 2008/0283754 | A1 | * | 11/2008 | Nerin ................ G01N 15/147 250/339.05 |
| 2009/0248318 | A1 | * | 10/2009 | Nagai ................ G01N 15/147 702/19 |
| 2012/0282601 | A1 | * | 11/2012 | Abe .................. G01N 15/1459 435/6.1 |
| 2014/0051071 | A1 | * | 2/2014 | Yoshida ................ G01N 21/51 435/6.1 |
| 2016/0061732 | A1 | * | 3/2016 | Yamada ............. G01N 33/80 435/288.7 |
| 2016/0091424 | A1 | * | 3/2016 | Yamada ............ G01N 15/1459 435/29 |
| 2016/0091484 | A1 | * | 3/2016 | Yamada ............ G01N 15/1436 356/40 |

FOREIGN PATENT DOCUMENTS

| | | |
|---|---|---|
| JP | H08-20442 A | 1/1996 |
| JP | 2006-292738 A | 10/2006 |
| WO | WO 2006/065987 A2 | 6/2006 |
| WO | WO 2010/056740 A1 | 5/2010 |

OTHER PUBLICATIONS

Reitz, S. et al., "Determination of Mirco-Litre Volumes With High Accuracy for Flow Cytometric Blood Cell Counting", *Measurement Science and Technology*, vol. 21, 2010, pp. 1-9.

* cited by examiner

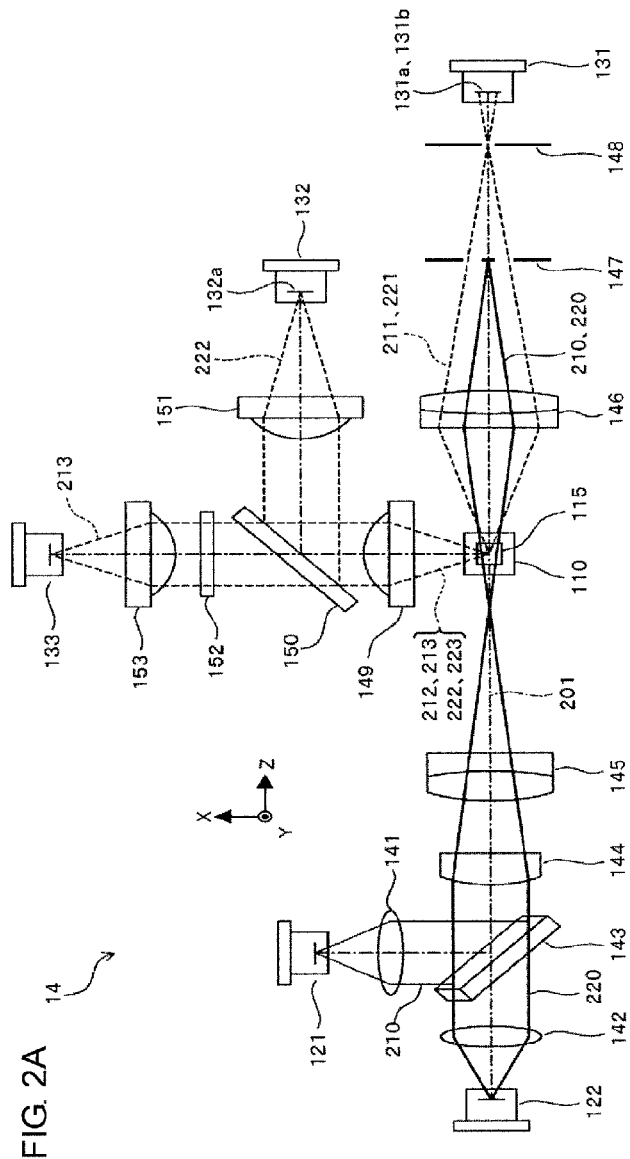

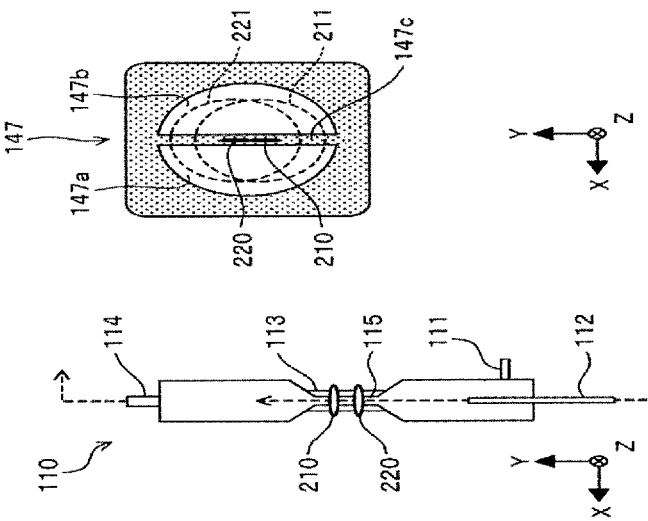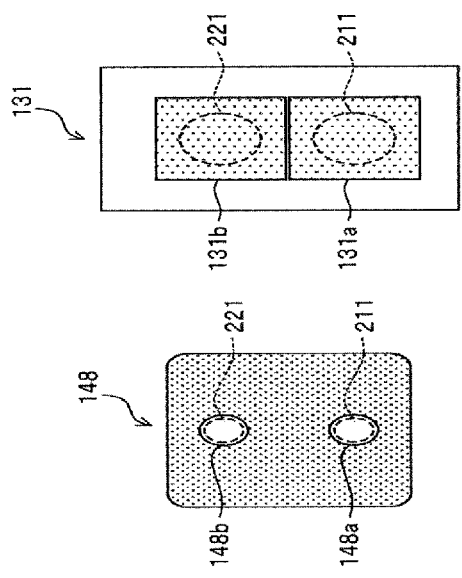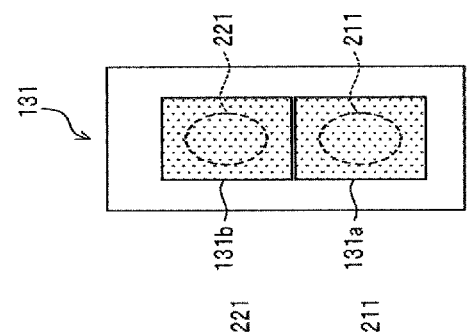

FIG. 4A When low concentration measurement samples were measured
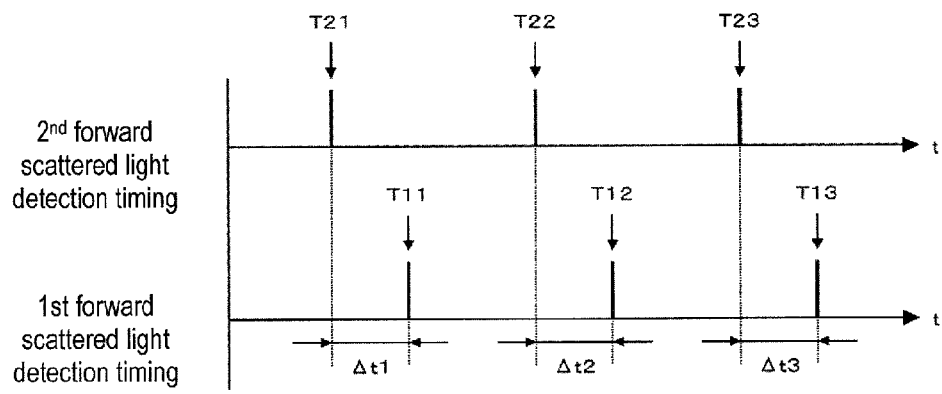
FIG. 4B When normal concentration measurement samples were measured
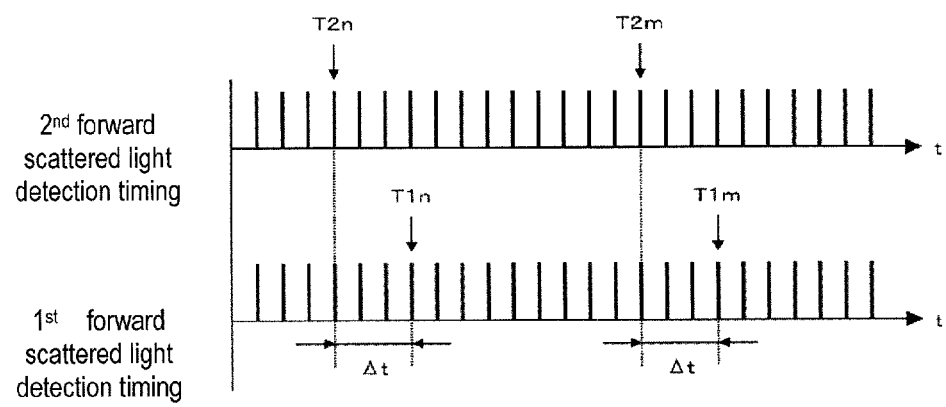

FIG. 9A  MCV
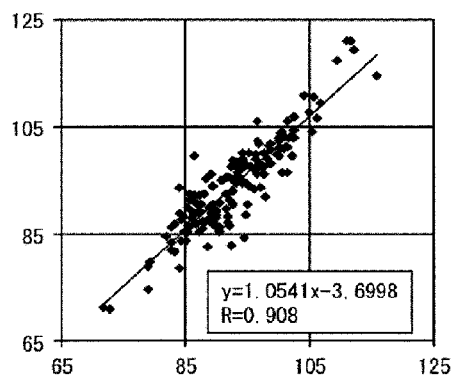
y=1.0541x-3.6998
R=0.908
FIG. 9B  MCHC
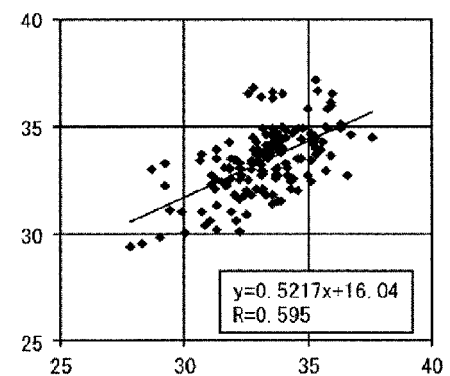
y=0.5217x+16.04
R=0.595
FIG. 9C  MCH
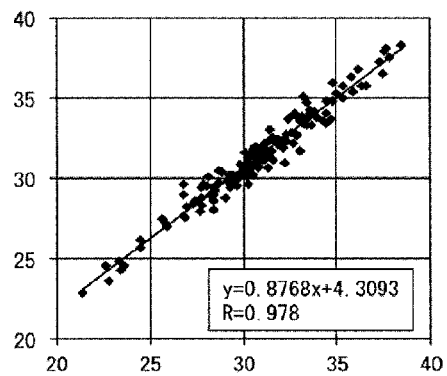
y=0.8768x+4.3093
R=0.978
FIG. 9D  HGB
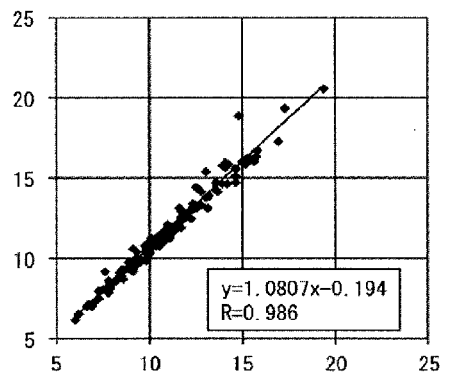
y=1.0807x-0.194
R=0.986

BLOOD ANALYZER AND BLOOD ANALYZING METHOD

RELATED APPLICATIONS

This application claims priority from prior Japanese Patent Application No. 2014-196279, filed on Sep. 26, 2014, entitled "BLOOD ANALYZER AND BLOOD ANALYZING METHOD".

BACKGROUND OF THE INVENTION

1. Field of the Invention

The present invention relates to a blood analyzer and a blood analyzing method.

2. Description of the Related Art

Blood analyzers configured to analyze blood samples generally perform measurements of blood cells such as red blood cells, white blood cells, platelets and the like. In order to perform measurements of these blood cells, the blood analyzer disclosed in Japanese Patent Application Publication No. 2006-292738, for example, is provided with a plurality of detection units which correspond to the measurement items, such as an RBC/PLT detection unit for measuring the number of red blood cells and the number of platelets, an HGB detection unit for measuring the hemoglobin content in the blood, and an optical detection unit for measuring the number of white blood cells.

It is desirable to suppress the size of the apparatus in order to control the surface area needed for installation of the blood analyzer in, for example, a research facility, while maintaining the measurability of the measurement items.

SUMMARY OF THE INVENTION

The scope of the present invention is defined solely by the appended claims, and is not affected to any degree by the statements within this summary.

The blood analyzer of a first aspect of the present invention is provided with a flow cell configured to flow a measurement sample containing blood cells, a first light source configured to irradiate light having a first wavelength on the measurement sample flowing through the flow cell, a second light source configured to irradiate a second light having a second wavelength which is different from the first wavelength on the measurement sample flowing through the flow cell, a first light receiving part configured to receive a first forward scattered light obtained by irradiating the first light on the blood cells flowing through the flow cell, a second light receiving part configured to receive a second forward scattered light obtained by irradiating the second light on the blood cells flowing through the flow cell, a processing unit configured to obtain values related to red blood cell count, white blood cell count, and hemoglobin based on a first scattered light information which is based on the signals output from the first light receiving part, and a second scattered light information which is based on the signals output from the second light receiving part.

The blood analyzing method of a second aspect of the present invention includes irradiating a first light having a first wavelength and irradiating a second light having a second wavelength which is different from the first wavelength on a measurement sample containing blood cells, receiving a first scattered light obtained by irradiating the first light on a blood cell, and receiving a second scattered light obtained by irradiating the second light on the blood cell, and obtaining values related to the number of red blood cells, the number of white blood cells, and hemoglobin based on the first scattered light information which is based on the first scattered light, and the second scattered light information which is based on the second scattered light.

BRIEF DESCRIPTION OF THE DRAWINGS

FIGS. 2A and 2B respectively are schematic views of the optical detection unit of the first embodiment viewed in the Y-axis negative direction and the X-axis positive direction;

FIG. 3A through 3D respectively are schematic views showing the structure of the flow cell, beam stopper, pinhole, and optical detecting unit of the first embodiment;

FIG. 4A illustrates detection timing when a low concentration measurement sample is measured, and FIG. 4B illustrates detection timing when a normal concentration measurement sample is measured;

FIG. 9A through 9D show the correlations of results from the first embodiment and results from a reference method;

DETAILED DESCRIPTION OF THE PREFERRED EMBODIMENTS

The first and second embodiments described below apply the present invention in an apparatus which performs examination and analysis of blood by detecting the white blood cells, red blood cells, platelets and the like contained in a blood sample, and counting each blood cell.

First Embodiment

Figure 1:
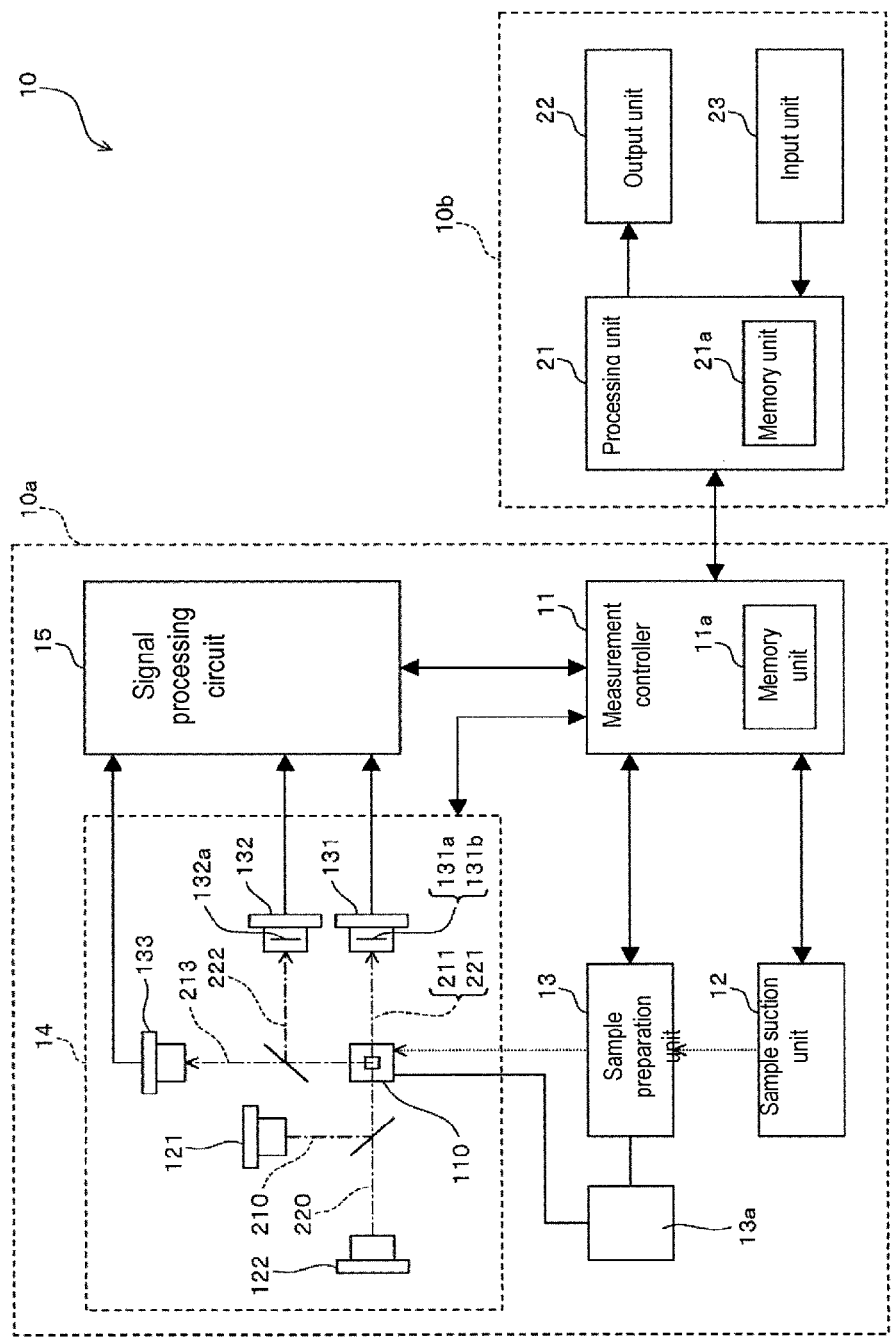
FIG. 1 is a block diagram showing the structure of the blood analyzer of a first embodiment.

As shown in FIG. 1, a blood analyzer 10 is provided with a measuring unit 10a and an information processing unit 10b. The measuring unit 10a is provided with a measurement controller 11, sample suction unit 12, sample preparing unit 13, optical detection unit 14, and signal processing circuit 15. The measurement controller 11 has a memory unit 11a. The information processing unit 10b is provided with a processing unit 21, output unit 22, and input unit 23. The processing unit 21 has a memory unit 21a.

The measurement controller 11 receives signals output from each part of the measuring unit 10a, and controls each part of the measuring unit 10a. The measurement controller 11 performs communications with the information processing unit 10b. The sample suction unit 12 suctions the blood sample from the sample container through a suction tube. A container holding reagent 13a is connected to the sample preparing unit 13. The reagent 13a is a diluting liquid. The reagent 13a is used as a sheath fluid to form a flow of measurement sample in the flow cell 110. The sample preparing unit 13 mixes the reagent 13a and the blood sample suctioned by the sample suction unit 12 to prepare the measurement sample. The shape of red blood cells in the blood sample becomes spherical through the reagent 13a. The preparation of the measurement sample is performed without using hemolytic agent and stain. The measurement sample contains the blood cells in the blood sample.

Optical detection unit 14 has a flow cell 110, first light source 121, second light source 122, and optical detectors 131 through 133. The first light source 121 irradiates light 210 having a first wavelength on the measurement sample flowing through the flow cell 110. The second light source 122 irradiates light having a second wavelength which is different from the first wavelength on the measurement sample flowing through the flow cell 110.

The optical detector 131 has a first light receiving part 131a and a second light receiving part 131b. The first light receiving part 131a receives a first scattered light obtained by irradiating the first light 210 on a blood cell flowing through the flow cell 110. The first scattered light is a first forward scattered light 211 in the first embodiment. The second light receiving part 131b receives a second scattered light obtained by irradiating the second light 220 on a blood cell flowing through the flow cell 110. The second scattered light is a second forward scattered light 221 in the first embodiment. The optical detector 132 has a light receiving part 132a. The light receiving part 132a receives a second side scattered light 222 obtained by irradiating the second light 220 on a blood cell flowing through the flow cell 110. The optical detector 133 receives a first fluorescent light 213 obtained by irradiating the first light 210 on a blood cell flowing through the flow cell 110.

The first scattered light also may be the first side scattered light 212 which is described below. That is, the first light receiving part 131a also may be arranged so as to receive the first side scattered light 212 as the first scattered light. The second scattered light also may be the second side scattered light 222. That is, the second light receiving part 131b also may be arranged so as to receive the second side scattered light 222 as the second scattered light.

The first light receiving part 131a outputs signals based on the first forward scattered light 211. The second light receiving part 131b outputs signals based on the second forward scattered light 221. The optical detector 131 sends the signals output from the first light receiving part 131a and the second light receiving part 131b to the signal processing circuit 15. The light receiving part 132a outputs signals based on the second side scattered light 222. The optical detector 132 sends the signals output from the light receiving part 132a to the signal processing circuit 15. The optical detector 133 sends the signals based on the first fluorescent light 213 to the signal processing circuit 15. The optical detection unit 14 is described below with reference to FIGS. 2A and 2B and FIG. 3A through 3D.

The signal processing circuit 15 extracts the waveforms corresponding to cells, and calculates the peak values, widths, areas and the like of the waveforms based on the signals output by the optical detectors 131 through 133. The signal processing circuit 15 calculates the peak value of the waveform obtained from the signal based on the first forward scattered light 211 as the first scattered light information. The signal processing circuit 15 calculates the peak value of the waveform obtained from the signal based on the second forward scattered light 221 as the second scattered light information. The signal processing circuit 15 calculates the peak value of the waveform obtained from the signal based on the second side scattered light 222 as the third scattered light information. The signal processing circuit 15 calculates the peak value of the waveform obtained from the signal based on the first fluorescent light 213 as the fluorescent light information.

When the first scattered light is designated as the first side scattered light 212, the first scattered light information becomes the peak value of the waveform obtained from the signals based on the first side scattered light 212. When the second scattered light is designated as the second side scattered light 222, the second scattered light information becomes the peak value of the waveform obtained from the signals based on the second side scattered light 222.

The signal processing circuit 15 outputs the first scattered light information, second scattered light information, third scattered light information, and fluorescent light information to the measurement controller 11. The measurement controller 11 stores the information output from the signal processing circuit 15 in a memory unit 11a. When the blood sample measurements end, the measurement controller 11 sends the first scattered light information, second scattered light information, third scattered light information, and fluorescent light information obtained for each blood cell to the information processing unit 10b as measurement data.

The processing unit 21 receives signals output from each part of the information processing unit 10b, and controls each part of the information processing unit 10b. The memory unit 21a stores a program which is executed by the processing unit 21, and various data. The memory unit 21a also is used as the work area of the processing unit 21. The processing unit 21 obtains values related to the red blood cell count, white blood cell count, and hemoglobin based on the first scattered light information and the second scattered light information. The processing unit 21 additionally classifies and counts the blood cells and obtains various values. The processes performed by the processing unit 21 are described below referring to FIG. 7.

The output unit 22 is a display which displays textual and graphic information. The input unit 23 is a keyboard and mouse which receive input from the operator.

As shown in FIGS. 2A and 2B, the optical detection unit 14 is provided with a flow cell 110, first light source 121, second light source 122, optical detectors 131 through 133, collimator lenses 141 and 142, dichroic mirror 143, cylindrical lens 144, collective lenses 145 and 146 Beam stopper 147, pinhole 148, collimator lens 149, dichroic mirror 150, collective lens 151, spectral filter 152, and collective lens 153. For the sake of convenience, the mutual intersection of the XYZ coordinate axes is shown in FIGS. 2A and 2B.

As shown in FIG. 3A, the flow cell 110 has a sheath fluid supply port 111, a sample nozzle 112, a pore part 113, and a disposal port 114. The sheath fluid supply port 111 supplies sheath fluid into the flow cell 110. The sample nozzle 112 injects a measurement sample in the Y-axis positive within the flow cell 110. The measurement sample progresses through a flow path 115 formed in the pore part 113 while encapsulated in the sheath fluid, and toward the disposal port 114. The flow path 115 extends in the Y-axis direction. The particles contained in the measurement sample pass through the flow path 115 in single file array.

Returning to FIGS. 2A and 2B, the first light source 121 emits a first light 210 in the X-axis negative direction. The first light 210 is laser light. The wavelength of the first light 210 is set at 400 nm or greater but not more than 435 nm. In the first embodiment, the wavelength of the first light 210 is approximately 405 nm. The first light source 121 is arranged so that the lamination direction of the semiconductor layers of the light emitting part (not shown in the drawing) matches the Z-axis direction. The spread angle of the first light 210 is greatest in the Z-axis direction and smallest in the Y-axis direction. The exit optical axis of the first light source 121 intersects the optical axis 201 of the collimator lens 142. The optical axis 201 is parallel to the Z-axis.

The second light source 122 emits the second light 220 in the Z-axis positive direction. The second light 220 is laser light. The wavelength of the second light 220 is set at 610 nm or greater but not more than 750 nm. In the first embodiment, the wavelength of the second light 220 is approximately 640 nm. The second light source 122 is arranged so that the lamination direction of the semiconductor layers of the light emitting part (not shown in the drawing) matches the X-axis direction. The spread angle of the second light 220 is greatest in the X-axis direction and smallest in the Y-axis direction. The exit optical axis of the second light source 122 matches the optical axis 201.

The collimator lens 141 converts the first light 210 to parallel light. The collimator lens 142 converts the second light 220 to parallel light. The dichroic mirror 143 reflects the first light 210 and transmits the second light 220. The dichroic mirror 143 is arranged so that the travel direction of the first light 210 reflected by the dichroic mirror 143 is inclined from the Z-axis direction slightly to the Y-axis direction, as shown in FIG. 2B.

The cylindrical lens 144 converges the first light 210 and second light 220 only in the X-axis direction. The collecting lens 145 converges the first light 210 and the second light 220 in the Y-axis direction, focusing on the position of the flow path 115 of the flow cell 110. The collecting lens 145 also converges the first light 210 and the second light 220 in the X-axis direction, focusing on the position on the Z-axis negative side of the flow path 115. Thus, the first light 210 and the second light 220 irradiate a narrow beam in the X-axis direction on the flow path 115, as shown in FIG. 3A.

As shown in FIG. 2B, since the first light 210 which is reflected by the dichroic mirror 143 travels in a direction slightly inclined to the Y-axis direction from the Z-axis direction, the irradiation position 202 of the first light 210 on the flow path 115 is shifted in the Y-axis direction from the irradiation position 203 of the second light 220. The irradiation position 203 of the second light 220 is on the optical axis 201.

When the first light 210 irradiates the blood cell at irradiation position 202, a first forward scattered light 211, first side scattered light 212, and first fluorescent light 213 are produced from the blood cell irradiated by the first light 210. The wavelength of the first forward scattered light 211 and the wavelength of the first side scattered light 212 are substantially the same as the wavelength of the first light 210. When the second light 220 irradiates the blood cell at irradiation position 203, a second forward scattered light 221, second side scattered light 222, and second fluorescent light 223 are produced from the blood cell irradiated by the second light 220. The wavelength of the second forward scattered light 221 and the wavelength of the second side scattered light 222 are substantially the same as the wavelength of the second light 220.

The first fluorescent light 213 and the second fluorescent light 223 are equivalent to autofluorescence since a staining agent is not used in the preparation of the measurement sample. In a second embodiment described later, eosinophils are classified based on the first fluorescent light 213 which is an autofluorescence produced by eosinophils.

The collective lens 146 has the function of correcting chromatic aberration relative to the first forward scattered light 211 and the second forward scattered light 221. The collective lens 146 converges the first forward scattered light 211 and the second forward scattered light 221 at the position of the pinhole 148. The collective lens 146 also converges part of the first light 210 and the second light 220 that does not irradiate a blood cell and is transmitted through the flow cell 110 at the position of the beam stopper 147. As shown in FIG. 2B, the optical axis of the collective lens 146 is shifted in the Y-axis direction from parallel to the Z-axis, that is shifted from the optical axis 201. Thus, after the light rays at the center of the first forward scattered light 211 are transmitted through the collective lens 146, the rays travel in a direction inclined slightly in the Y-axis negative direction from the Z-axis positive direction. After the light rays at the center of the second forward scattered light 221 are transmitted through the collective lens 146, the rays travel in a direction inclined slightly in the Y-axis positive direction from the Z-axis positive direction.

As shown in FIG. 3B, the beam stopper 147 has apertures 147a and 147b, and a light shield part 147c. The apertures 147a and 147b are semicircular in shape. The light shield part 147c is formed between the aperture 147a and the aperture 147b. The beam stopper 147 is configured by a thin plate member which is impenetrable to light. The beam stopper 147 is arranged at the focus position in the X-axis direction of the first light 210 and the second light 220. Thus, the first light 210 and the second light 220 become narrow beam shapes in the Y-axis direction on the light shield part 147c, and are blocked by the light shield part 147c. The majority of the first forward scattered light 211 and the second forward scattered light 221 pass through the beam stopper 147 through the apertures 147a and 147b.

As shown in FIG. 3C, the pinhole 148 has two holes 148a and 148b aligned in the Y-axis direction. The first forward scattered light 211 converges at the position of the hole 148a, and the second forward scattered light 221 converges at the position of the hole 148b. The first forward scattered light 211 and the second forward scattered light 221 pass through the holes 148a and 148b, respectively.

As shown in FIG. 3D, the optical detector 131 is a photodiode. The first light receiving part 131a and the second light receiving part 131b are arranged on the same plane. The optical detector 131 outputs signals based on the first forward scattered light 211 which irradiates the first light receiving part 131a, and signals based on the second forward scattered light 221 which irradiates the second light receiving part 131b.

Returning to FIG. 2A, the collimator lens 149 converts the first side scattered light 212, second side scattered light 222, first fluorescent light 213, and second fluorescent light 223 to parallel light. The optical axis of the collimator lens 149 matches a line parallel to the X-axis through the flow path 115 of the flow cell 110. The dichroic mirror 150 reflects the second side scattered light 222 in the Z-axis positive direction, and transmits the first side scattered light 212, first fluorescent light 213, and second fluorescent light 223.

The collective lens 151 converges the second side scattered light 222 reflected by the dichroic mirror 150. The optical detector 132 is a photodiode. The optical detector 132 outputs signals based on the second side scattered light which irradiates the light receiving part 132a. The spectral filter 152 absorbs the first side scattered light 212 and the second fluorescent light 223, and transmits the first fluorescent light 213. The collective lens 153 converges the first fluorescent light 213 which is transmitted through the spectral filter 152. The optical detector 133 is an avalanche photodiode. The optical detector 133 outputs signals based on the first fluorescent light 213.

The method of associating the first scattered light information and the second scattered light information is described below.

As described referring to FIG. 2B, the irradiation position 202 of the first light 210 and the irradiation position 203 of the second light 220 are mutually shifted in the Y-axis direction. The blood cells within the flow path 115 flow from the irradiation position 203 to the irradiation position 202. Accordingly, there is a predetermined timing from the irradiation of the blood cell by the second light 220 at the irradiation position 203, until the same blood cell is irradiated by the first light 210 at the irradiation position 202. When the first scattered light information based on the first forward scattered light 211 produced by the first light 210, and the second scattered light information based on the second forward scattered light 221 produced by the second light 220 are used in analysis, the first scattered light information and the second scattered light information produced from the same blood cell therefore must be mutually associated.

As shown in FIG. 4A, when a low concentration measurement sample is measured, the detection timing of the second forward scattered light 221 and the detection timing of the first forward scattered light 211 become discrete. In this case the detection timing of the second forward scattered light 221 based on the next blood cell cannot be started during the interval between the detection timing of the second forward scattered light 221 and the detection timing of the first forward scattered light 211 based on a single blood cell. Accordingly, the detection timing of the first forward scattered light 211 arriving subsequent to the detection timing of the second forward scattered light 221 can be associated as a detection timing related to the same blood cell.

In the example of FIG. 4A, the detection timings T21 through T23 are respectively associated with the detection timings T11 through T13. The time differential of the detection timings based on the same blood cell is substantially the same whatever the blood cell. Accordingly, for example, the time differentials Δt1, Δt2, Δt3 of two mutually associated detection timings are obtained, and a time differential Δt is calculated by averaging the time differentials. Hence, the time differential Δt can be used as the time differential of the detection timings of the second forward scattered light 221 and the first forward scattered light 211 relative to each blood cell.

As shown in FIG. 4B, when a normal concentration measurement sample is measured, the detection timing of the second forward scattered light 221 and the detection timing of the first forward scattered light 211 are mixed. In this case it is difficult to associate the detection timing of the second forward scattered light 221 and the detection timing of the first forward scattered light 211 based on the same blood cell. However, the speed of the measurement sample flowing through the flow cell 110 is approximately the same when the concentration is high and when the concentration is low. The time differential Δt obtained when the concentration was low can be used as the time differential of the detection timing of the second forward scattered light 221 and the detection timing of the first forward scattered light 211 based on the same blood cell when concentration is high. In the example of FIG. 4B, the detection timings T2n and T2m are associated with the detection timings T1n and T1m, respectively, using the time differential Δt.

In the first embodiment, an advance time differential Δt is obtained beforehand by flowing a low concentration sample through the flow cell 110 before performing a measurement; the second scattered light information and the first scattered light information based on the same blood cell are then sequentially associated using the time differential Δt during the actual measurement. Similarly, the second scattered light information and the fluorescent light information based on the same blood cell are sequentially associated using the time differential Δt during the actual measurement. In this way all information based on the same blood cell can be associated by using the time differential Δt obtained beforehand.

The difference of the first forward scattered light 211 produced from red blood cells and the first forward scattered light 211 produced from blood cells other than red blood cells is described below. Blood cells other than red blood cells include white blood cells and platelets.

The scattered light produced from particles which are irradiated by light is determined by the particle diameter and refractive index according to the Mie scattering theory. The refractive index can be expressed by complex number consisting of a real number part and an imaginary number part. That is, when the complex refractive index is designated m, the refractive index is designated nr, and the absorption is designated ni, the complex refractive index m can be calculated by the following equation.

$$m = nr + ini$$

According to the above equation, the refractive index may differ according to differences in the degree of absorption of the particle relative to light since the complex refractive index m changes according to the absorption ni. Thus, when different types of particles have mutually different degrees of absorption and these particles are irradiated by light, the resultant scattered light also will be mutually different.

Figure 5A:
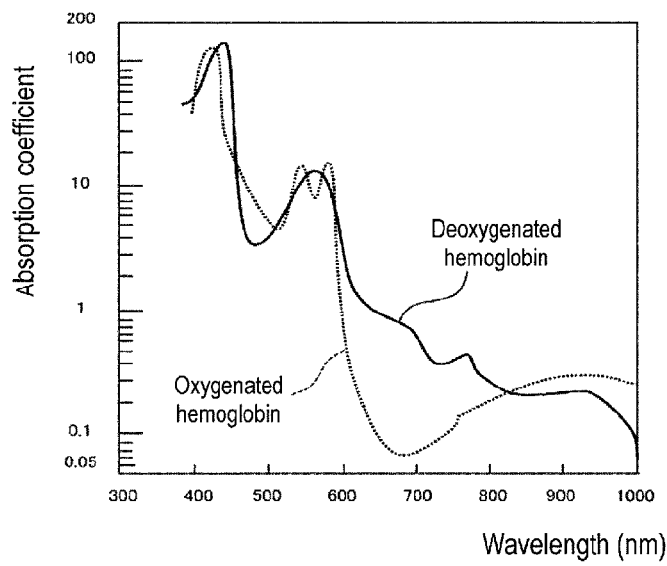
FIG. 5A shows the absorption characteristics of the hemoglobin contained in a red blood cell.

Hemoglobin which is contained in red blood cells has the absorption characteristics shown in FIG. 5A. In FIG. 5A, the horizontal axis represents the wavelength of the light irradiated on the hemoglobin, and the vertical axis represents the absorption coefficient. FIG. 5A shows the absorption coefficients of oxygenated hemoglobin and deoxygenated hemoglobin, respectively. The hemoglobin in red blood cells is a mixture of oxygenated hemoglobin and deoxygenated hemoglobin, and generally the oxygen saturation of venous blood hemoglobin is 75%, that is, content ratio of oxygenated hemoglobin to deoxygenated hemoglobin is 3:1. Therefore, the properties of oxygenated hemoglobin are dominant in red blood cells contained in the blood sample.

The absorption coefficient of oxygenated hemoglobin increases in several stages in the wavelength range of 400 nm or greater but not more than 435 nm compared to other wavelength bands. On one hand, the absorption coefficient of oxygenated hemoglobin decreases in several stages in the wavelength range of 610 nm or greater but not more than 700 nm compared to other wavelength bands. That is, there is a large difference in the degree of absorption of red blood cells relative to the first light 210 and the degree of absorption of red blood cells relative to the second light 220. On the other hand, there is a small difference in the degree of absorption of blood cells other than red blood cells relative to the first light 210 and the degree of absorption of blood cells other than red blood cells relative to the second light 220 because blood cells other than red blood cells do not contain hemoglobin.

From the above, there is a marked difference in the degree of absorption relative to the first light 210 and the degree of absorption relative to the second light 220 between red blood cells and blood cells other than red blood cells. Accordingly, there also is a difference in the intensity of the first forward scattered light 211 produced by irradiation with the first light 210 and the intensity of the second forward scattered light 221 produced by irradiation with the second light 220 between the red blood cells and the blood cells other than red blood cells. Specifically, in red blood cells the first forward scattered light is easily weaker than the second forward scattered light. In blood cells other than red blood cells the first forward scattered light and the second forward scattered light are easily substantially the same.

A simulation of the particle analysis is described below.

The present simulation was performed under the following conditions. The NA of the optical system receiving the forward scattered light is set at NA=0.22. An optical systems provided with the collective lens 146 Beam stopper 147, pinhole 148, and optical detector 131 is used as the optical system which receives the forward scattered light. The light shield part 147c of the beam stopper 147 has a width of 0.3 mm in the X-axis direction. The distance between the flow cell 110 and the beam stopper 147 is 6 mm. The first light 210 and the second light 220 which irradiate the flow cell 110 have a width of 10 μm in the Y-axis direction. In the present simulation, 81 cell-like particles having the same characteristics as red blood cells and 4 cell-like particles having the same characteristics as platelets were set. The intensities of the forward scattered light produced by irradiating laser light of a predetermined wavelength on these particles was calculated by the simulation.

In the present simulation particles corresponding red blood cells and platelets were irradiated with a first light 210 at a wavelength of 405 nm, and a second light 220 at a wavelength of 640 nm. The first scattered light information and the second scattered light information corresponding to each particle obtain in this way were plotted on scattergram 300 shown in FIG. 5B. The horizontal axis and vertical axis of the scattergram 300 respectively represent the first scattered light information and the second scattered light information.

Then, a map 310 was created on the scattergram 300 based on the particles corresponding to red blood cells. The two axes of map 310 are the red blood cell volume and hemoglobin concentration. The map 310 is created based on the values of red blood cell volume V30 through V150 and the values of hemoglobin concentration HC22 through HC46 for 81 individual particles. The intersection points of the grid of map 310 are the positions at which each particle was plotted. The map 310 corresponds to the range of red blood cell distribution. For the red blood cells of healthy persons, the red blood cell volume is V60 through V120 and the hemoglobin concentration is HC31 through HC37. Then, a distribution line 320 was created on the map 310 based on the particles corresponding to platelets. The distribution line 320 is created based on four particles having a volume value from V0.5 through V33.

From the results of the present simulation the red blood cells collected from subjects can be considered to be distributed within the map 310, and the platelets collected from subjects can be considered to be on the distribution line 320.

In the results of the present simulation the map 310 representing the distribution of red blood cells is positioned to the upper left of the distribution line 320 representing the distribution of platelets, and there is no overlap of the map 310 and the distribution line 320. As described above, the first light 210 is absorbed by the hemoglobin contained in the red blood cells, and the first scattered light information is considered to be smaller than the second scattered light information. When the volume of the platelets collected from subjects is large, the platelets are positioned at extension line 321 of the distribution line 320. However, the platelets on the extended line 321 do not overlap the map 310 since there is no overlap of the map 310 and the extension line 321. Accordingly, red blood cells and platelets can be discriminated with high accuracy even when the volume of the platelets is large based on the results of the present simulation.

The platelets and the white blood cells are considered to have a generally similar refractive index, and have a similar property in that they do not have hemoglobin. Therefore, white blood cells also are generally considered to be distributed on the distribution line 320 and the extension line 321. Since white blood cells are larger than platelets, white blood cells are positioned in the region having larger first scattered light information and second scattered light information than platelets. Accordingly, red blood cells and white blood cells can be discriminated with high accuracy since white blood cells are unlikely to overlap the map 310 based on the results of the present simulation.

It is therefore understood that when the first light 210 and second light 220 are used as in the first embodiment, red blood cells, white blood cells, and platelets can be classified with high accuracy.

Figure 6A:
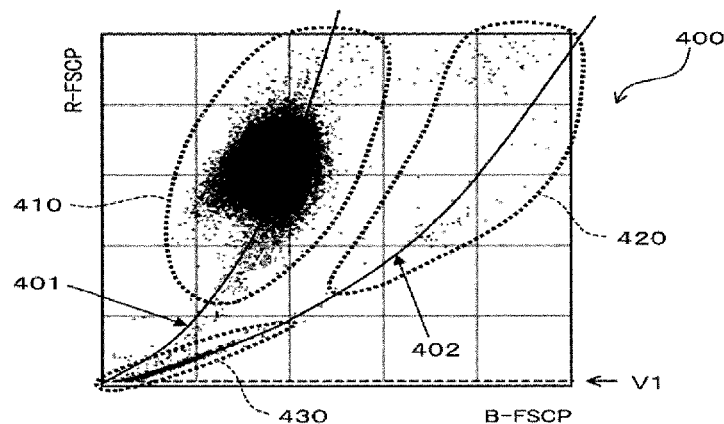
FIG. 6A is a scattergram for classifying red blood cells, white blood cells, and platelets in the first embodiment.

In the first embodiment red blood cells, white blood cells, and platelets are classified using regions 410, 420, and 430, as shown in FIG. 6A. Each blood cells is plotted in scattergram 400 based on the first scattered light information and second scattered light information obtained from each blood cell. The horizontal axis and vertical axis of the scattergram 400 respectively represent the first scattered light information and the second scattered light information. Regions 410, 420, and 430 are regions in which red blood cells, white blood cells, and platelets are distributed, respectively. The area in which the second scattered light information is less than a threshold value V1 in scattergram 400 is excluded.

As shown in FIG. 6A, red blood cells are distributed along a distribution curve 401, and white blood cells and platelets are distributed along a distribution curve 402. The distribution curve 402 corresponds to the distribution line 320 and the extension line 321 of FIG. 5B. In actual measurement values, therefore, regions 410, 420, and 430 are unlikely to overlap because the distribution curves 401 and 402 extend at mutually different angles without intersection.

Figure 5B:
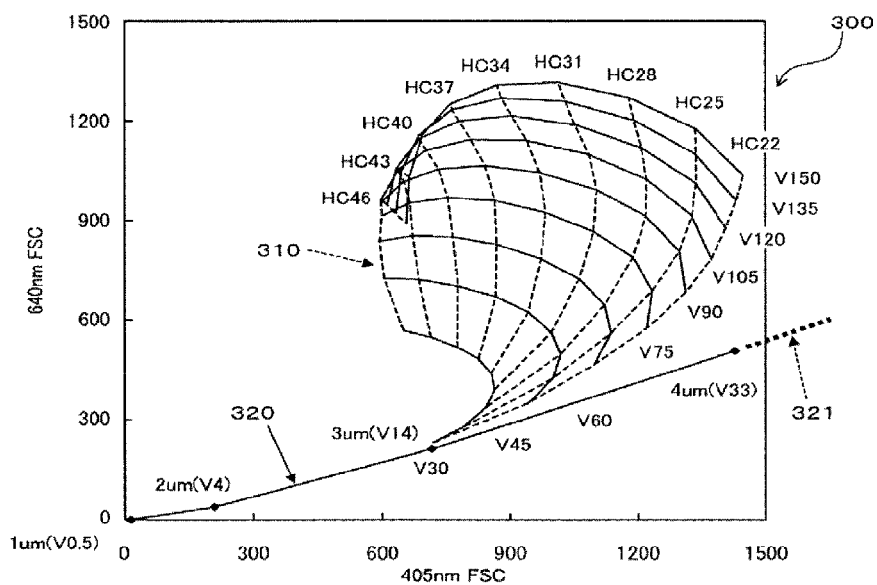
FIG. 5B shows the simulation results of particle analysis.
Figure 6B:
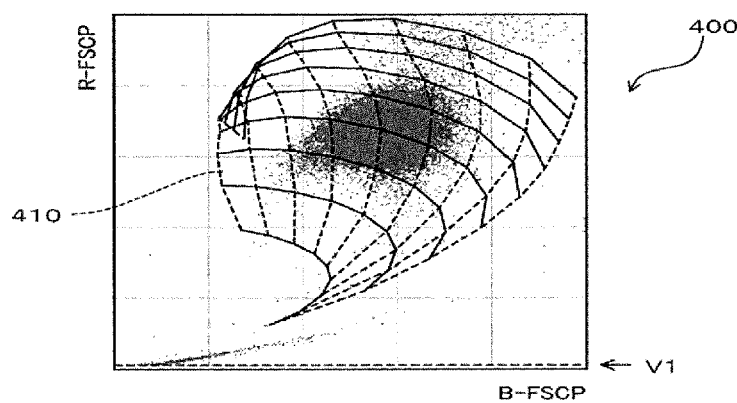
FIG. 6B is a scattergram combining the map information in the first embodiment.

The map 310 shown in FIG. 5B was created based on 81 individual particles which had similar properties as red blood cells, red blood cell volume values of V30 through V150, and hemoglobin concentration values of HC22 through HC46. Accordingly, the red blood cell volume and hemoglobin concentration can be obtained for each blood cell within region 410 by combining the map information representing red blood cell volume and hemoglobin concentration in the region 410 which corresponds to red blood cells in the scattergram 400, as shown in FIG. 6B. Note that FIG. 6B shows an area in which the first scattered light information is small in the scattergram 400 of FIG. 6A.

Specifically, the region 410 which includes map information is applied to the scattergram 400 obtained by actual measurements, as shown in FIG. 6B. Region 410 is developed together with blood cells contained in region 410 to create the scattergram 500 shown in FIG. 6C, and the red blood cell volume and hemoglobin concentration is obtained for each blood cell based on the plot position on the scattergram 500. In scattergram 500, the horizontal axis represents the hemoglobin concentration and the vertical axis represents the red blood cell volume.

More specifically, the memory unit 21a of the processing unit 21 stores the conversion information. The conversion information is configured from a conversion table and conversion program. The conversion table is a table representing the 81 individual intersection points within the region 410 shown in FIG. 6B plotted at positions in the scattergram 500 shown in FIG. 6C. The conversion program is a program configured to convert particles positioned between the intersection points of region 410 shown in FIG. 6B to positions on the scattergram 500 based on the distance to the intersection point. That is, the conversion information is information regulating the relationship between the combination of the first scattered light information and second scattered light information, and the combination of the red blood cell volume and hemoglobin concentration. The processing unit 21 obtains the red blood cell volume and the hemoglobin concentration from the first scattered light information and the second scattered light information using the conversion information.

The conversion information also may be configured from the conversion table alone. In this case the conversion table is a table representing most intersection points plotted at positions on the scattergram 500 when the inter grid space of the region 410 shown in FIG. 6B is further divided by a predetermined number. In this case conversion accuracy is increased regardless of the increase in volume of the conversion information by easily increasing the number to be divided.

The process performed by the blood analyzer 10 is described below referring to FIG. 7. Steps S11 through S17 in FIG. 7 are performed under the control of the measurement controller 11, and steps S21 through S24 are performed under the control of the processing unit 21.

When the blood analyzer 10 starts, an advance time differential Δt is obtained as described referring to FIGS. 4A and 4B. The obtained advance time differential Δt is stored in the memory unit 11a of the measuring unit 10a.

Figure 7:
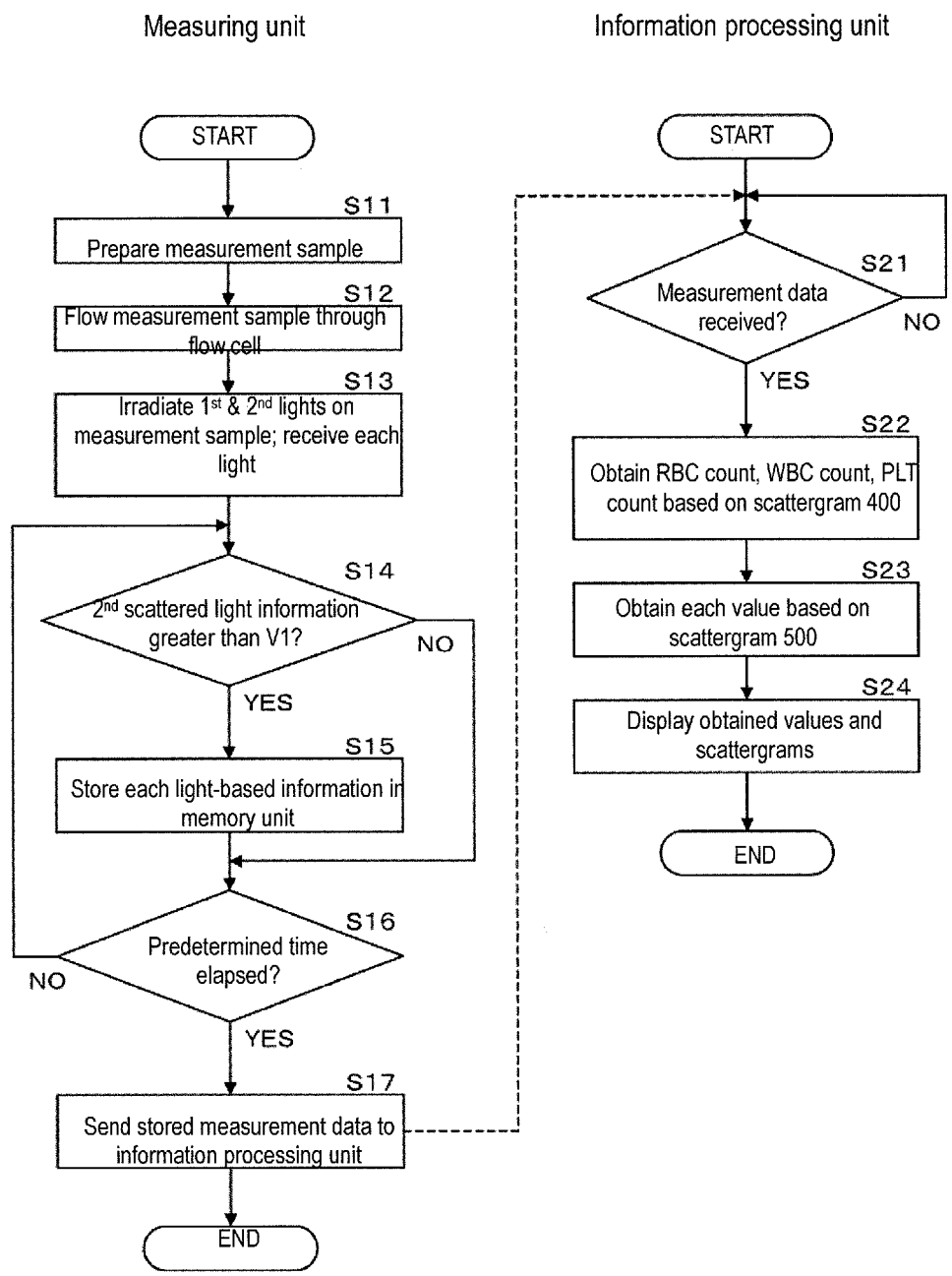
FIG. 7 is a flow chart showing the processes of the blood analyzer of the first embodiment.

As shown in FIG. 7, a blood sample and reagent 13a are mixed to prepare a measurement sample in step S11. The preparation of the measurement sample at this time is performed without mixing a hemolytic agent and staining agent.

In step S12, the measurement sample flows through the flow cell 110. In step S13, the first light 210 and the second light 220 irradiate the measurement sample flowing through the flow cell 110. The first forward scattered light 211 and the first fluorescent light 213 obtained by irradiating blood cells flowing through the flow cell 110 with the first light 210 are received by the first light receiving part 131a and the fluorescent light detector 133. The second forward scattered light 221 and the second side scattered light 222 obtained by irradiating blood cells flowing through the flow cell 110 with the second light 220 are received by the second light receiving part 131b and the light receiving part 132a.

In step S14, the measurement controller 11 determines whether the second scattered light information is greater than the threshold value V1 shown in FIG. 6A. The threshold value V1 is preset at a minute value, and is used to eliminate signals which include noise. When the determination is YES in step S14, the measurement controller 11 mutually associates the first scattered light information, second scattered light information, third scattered light information, and fluorescent light information produced from the same blood cell based on the time differential Δt, and stores the associated information in the memory unit 11a in step S15. When the determination is NO in step S14, the measurement controller 11 advances the process to step S16 without storing the blood cell information this time.

In step S16, the measurement controller 11 determines whether a predetermined time has elapsed since step S14 first started. The measurement controller 11 repeats the processes of steps S14 and S15 for each blood cell until the predetermined time has elapsed. When the determination is YES in step S16, the measurement controller 11 sends the measurement data stored in the memory unit 11a to the information processing unit 10b in step S17.

In step S21, the processing unit 21 determines whether measurement data have been received from the measuring unit 10a. When the determination is YES in step S21, the processing unit counts the number of blood cells in regions 410, 420, and 430 and obtains red blood cell count, white blood cell count, and platelet count, respectively, in step S22 based on the scattergram 400 shown in FIG. 6A.

In step S22, for the convenience of the description, regions 410, 420, and 430 are set on scattergram 400, and the number of blood cells in regions 410, 420, and 430 are counted. However, scattergram 400 and regions 410, 420, and 430 need not necessarily be created inasmuch as the number of blood cells in regions 410, 420, and 430 also may be obtained by data processing.

The same applies to the following processes. That is, even in step S23 the scattergram 500 need not necessarily be created inasmuch as the data also can be obtained through data processing. Further, scattergram 400 and regions 410 and 430 need not necessarily be created in step S201 inasmuch as the number of blood cells in regions 410 and 430 also may be obtained by data processing. Still further, scattergram 700 and regions 710, 711, 712, and 713 need not necessarily be created in step S202 inasmuch as the number of blood cells in regions 710, 711, 712, and 713 also may be obtained by data processing. Additionally, scattergram 730 and region 731 need not necessarily be created in step S203 inasmuch as the number of blood cells in region 731 also may be obtained by data processing.

Figure 6C:
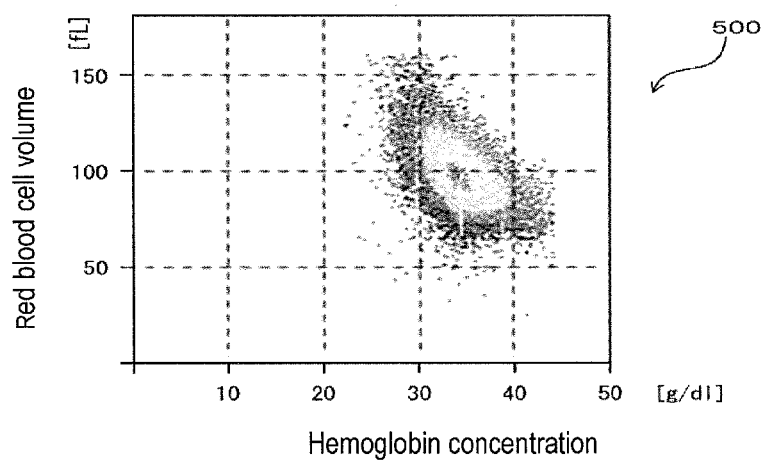
FIG. 6C is a scattergram plotting red blood cell volume and hemoglobin concentration on two axes in the first embodiment.

Then, in step S23, the processing unit 21 converts region 410 of scattergram 400 to scattergram 500 shown in FIG. 6C using the conversion information. The processing unit the red blood cell volume and hemoglobin concentration for each red blood cell in the region 410 in this way.

In step S23, the processing unit 21 also obtains each of the following values. The processing unit 21 determines the mean corpuscular volume (MCV) and mean corpuscular hemoglobin concentration (MCHC) using the red blood cell count obtained in step S22 as RBC. The MCV is calculated by dividing the total red blood cell volume of all particles in the scattergram 500 by the RBC. The MCHC is calculated by dividing the total hemoglobin concentration of all particles in the scattergram 500 by the RBC. The processing unit 21 calculates mean corpuscular hemoglobin (MCH) by MCV×MCHC. The processing unit 21 calculates hematocrit value (HCT) by MCV×RBC. The processing unit 21 calculates hemoglobin content (HGB) by HCT×MCHC. HGB also can be calculated by MCH×RBC.

Thus, the processing unit 21 obtains values relating to hemoglobin, that is, MCHC, MCH, and HGB, and obtains values relating to red blood cell volume, namely, MCV, MCH, and HCT.

Figure 8:
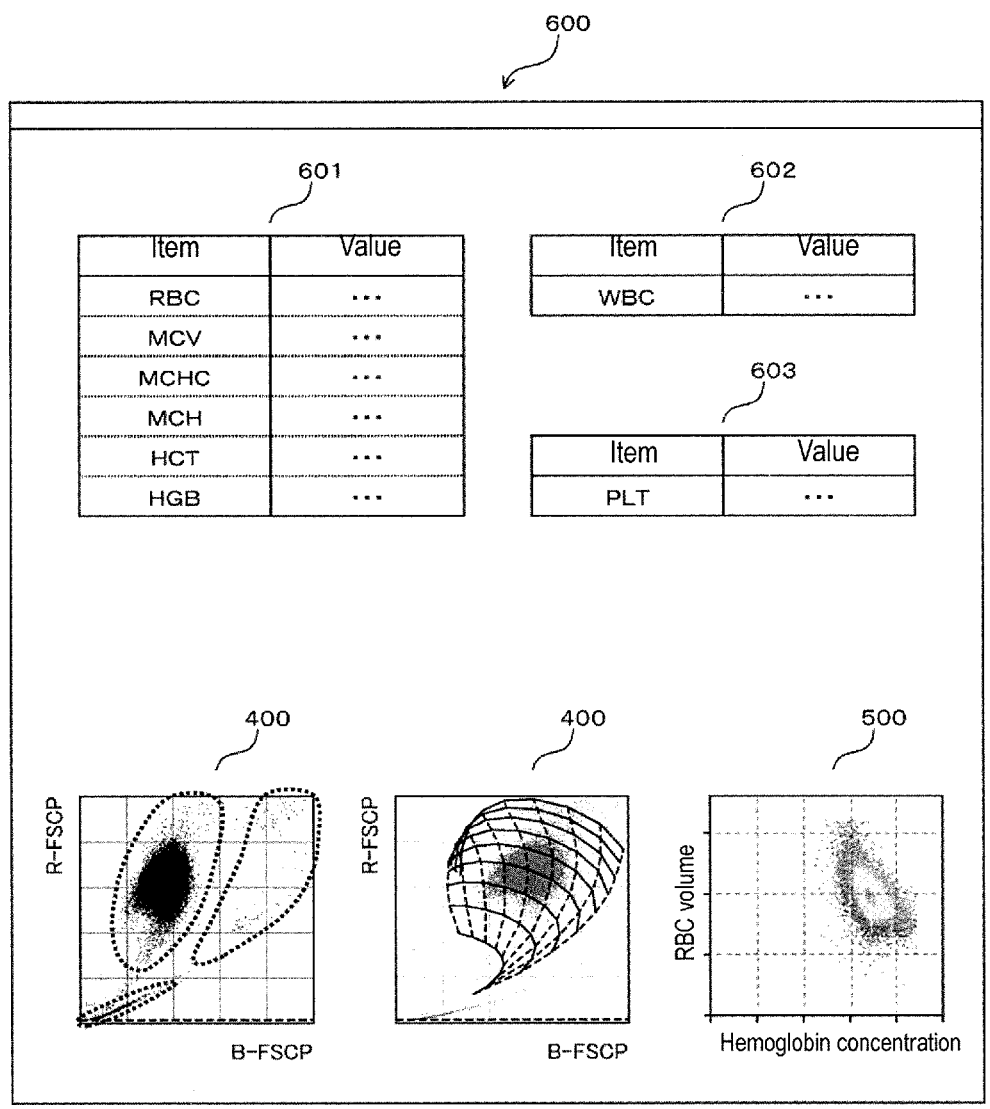
FIG. 8 shows a screen shown on the output unit of the first embodiment.

In step S24, the processing unit 21 displays a screen 600 shown in FIG. 8 on the output unit 22. The screen 600 includes lists 601 through 603, scattergram 400 shown in FIGS. 6A and 6B, and scattergram 500 shown in FIG. 6C. The lists 601 through 603 include values obtained in steps S22 and S23. The operator can visually comprehend the measurement results by referring to screen 600. The screen 600 may include, not only scattergram of two axes as shown in FIG. 8, but also may include scattergrams of three axes by adding an axis for an additional parameter.

According to the first embodiment, the processing unit 21 calculates the red blood cell volume and hemoglobin concentration for each blood cell, creates scattergram 500, and displays the data on the output unit 22. Although the hemoglobin was measured by lysing red blood cells in a reference method which will be described later, higher precision analysis is possible because the analysis is based on individual signals for each blood cell in the first embodiment. Where each blood cell is distributed also can be comprehended from the scattergram 500 which shows the red blood cell volume and hemoglobin concentration. The operator also can make judgements related to the measured sample from the distribution information of the red blood cells.

According to the first embodiment, red blood cells, white blood cells, and platelets can be classified and values related to hemoglobin can be obtained using the optical detection unit 14 to measure blood cells in a measurement sample prepared without hemolysis and staining. In this way the cost required for measurements can be reduced and the environmental burden can be mitigated since hemolytic agent and staining agent are unnecessary. Since only reagent 13a, a diluting liquid, is provided as a reagent of the blood analyzer 10, the cost required for measurements can be further reduced and the environmental burden can be further mitigated.

According to the first embodiment, the blood analyzer 10 is made more compact because it is unnecessary to provide a special detection unit for detecting hemoglobin, and it is unnecessary to provide a detection unit for measuring red blood cells and platelets. The blood analyzer 10 is made more compact because a detection unit for classifying white blood cells and a detection unit for measuring hemoglobin are not separately arranged, and the optical detection unit 14 is used jointly for white blood cell classification and for hemoglobin measurement.

The accuracy of actually obtained MCV, MCHC, MCH, and HGB is verified.

In this verification the results obtain via the first embodiment based on 156 Blood samples collected from different subjects were compared with results obtained by a comparative method of performing measurements by preparing measurement samples for each measurement item using reagents including hemolytic agent and staining agent and using an RBC/PLT detection unit, HGB detection unit and optical detection unit for measuring the number of white blood cells. In the reference method measurements were performed using a multi-function automatic blood analyzer XN-1000 manufactured by Sysmex Corporation.

The vertical axis in FIG. 9A through 9D respectively represent values obtained by the first embodiment. The horizontal axis in FIGS. 9A and 9B respectively represent values obtained by the reference method. Values from the first embodiment and values from the reference method were set as parameters, and the points corresponding to 156 Blood samples were plotted on the graphs of FIG. 9A through 9D. The graphs of FIG. 9A through 9D show an approximation line of the points corresponding to the 156 Blood samples. FIG. 9A through 9D show the values of correlation coefficient R and the results from the first embodiment and results from the reference method, and equations of the approximation lines when the horizontal axis is designated x and the vertical axis is designated y. The slope of the approximation line and the value of the correlation coefficient invariably approach [1], and the correlation of the results from the first embodiment and the results from the reference method increases.

As shown in FIGS. 9A, 9C, and 9D, the correlation of MCV, MCH, and HGB in the results from the first embodiment and results from the reference method is relatively high. On the other hand, there is a slightly lower correlation of MCH in the results of the first embodiment and results of the reference method, as shown in FIG. 9B. However, in the case of the first embodiment the MCH calculated by MCV× MCHC has a higher correlation than does MCV and MCH, and HGB calculated by MCH×RBC has a higher correlation than does MCH. HGB also has a higher clinical importance than MCHC. The results from the first embodiment can be said to have a usable level of accuracy to replace the results from the reference method in which the measurement samples were prepared using reagents such as hemolytic agent and staining agent.

Second Embodiment

In the second embodiment, after a measurement sample is prepared without performing hemolysis and staining similar to the first embodiment, the measurement sample flows through the flow cell 110 and sequentially subjected to processing to obtain information of red blood cells and platelets, and processing to obtain information of white blood cells. In the second embodiment, the structure of the blood analyzer 10 is identical to that of the first embodiment, and the processing performed by the blood analyzer 10 is partially changed from that of the first embodiment as will be described below.

In the case of the second embodiment, classification of red blood cells and platelets is performed by setting regions 410 and 430 in the scattergram 400 of FIG. 6A the same as in the first embodiment. However, classification of white blood cells is accomplished by obtaining only blood cells for which the first scattered light information is greater than the threshold value V2, and creating the scattergram 700 shown in FIG. 10A. The horizontal axis and the vertical axis of the scattergram 700 are the same as the scattergram 400. White blood cells are classified using region 710 set in the scattergram 700. Lymphocytes, monocytes and granulocytes also are classified using regions 711, 712, and 713 set within region 710.

Figure 10A:
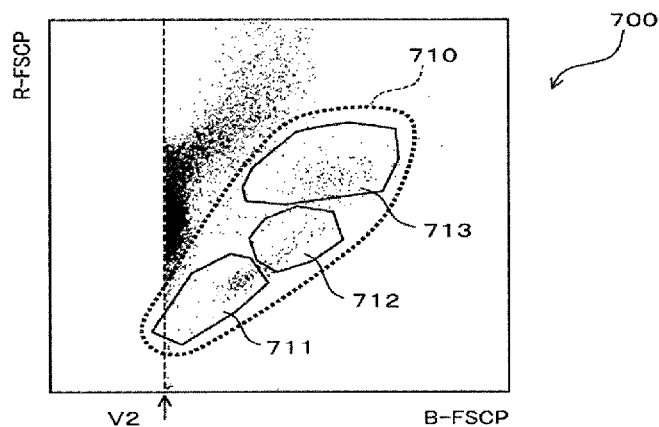
FIG. 10A is a scattergram for classifying white blood cells of a second embodiment.
Figure 10B:
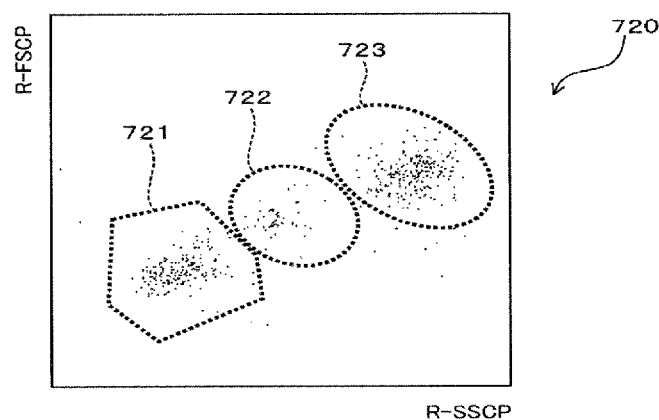
FIG. 10B is a scattergram for classifying white blood cells of a modification of the second embodiment.

Classification of lymphocytes, monocytes, and granulocytes also may be performed by creating a scattergram 720 shown in FIG. 10B based on blood cells within region 710. The horizontal axis and vertical axis of the scattergram 720 respectively represent the third scattered light information and the first scattered light information. The regions 721, 722, and 723 set in scattergram 720 are regions which classify lymphocytes, monocytes, and granulocytes, respectively.

Figure 10C:
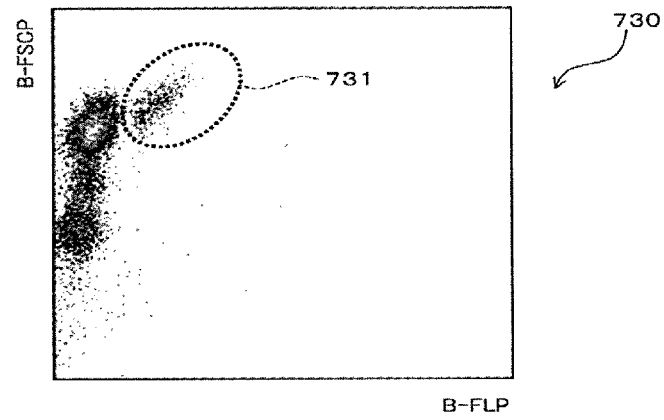
FIG. 10C is a scattergram for classifying eosinophils of the second embodiment.

A scattergram 730 also is created based on blood cells in region 710 in scattergram 700. The horizontal axis and vertical axis of the scattergram 730 respectively represent the fluorescent light information and the first scattered light information. Eosinophils are classified using region 731 set in the scattergram 730. Eosinophils are distributed in a region of greater fluorescent light information than other white blood cells in scattergram 730, as shown in FIG. 10C. The vertical axis of scattergram 730 also may represent the second scattered light information.

Figure 11:
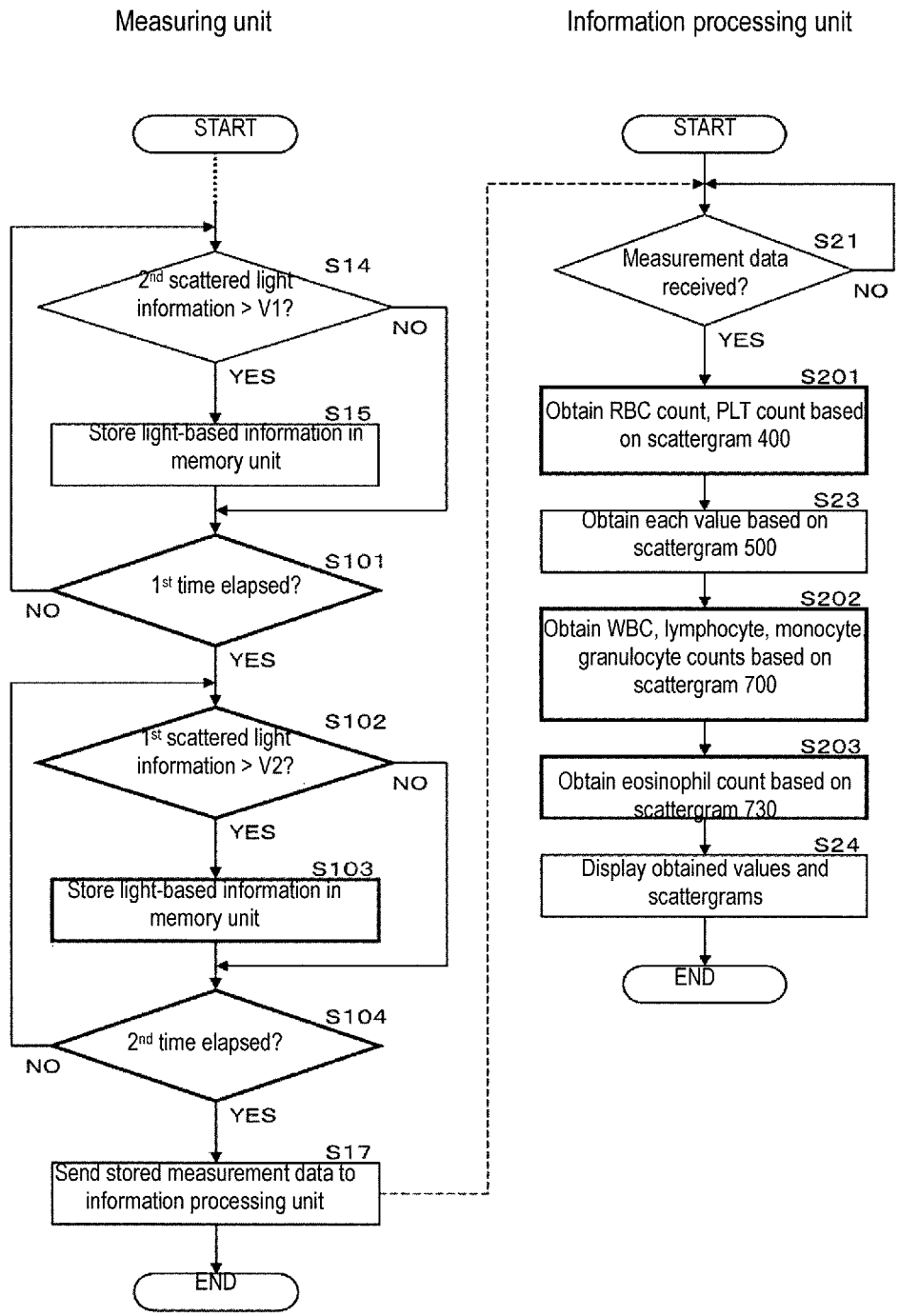
FIG. 11 is a flow chart showing the processes of the blood analyzer of the second embodiment.

As shown in FIG. 11, the processing performed by the measuring unit 10a of the second embodiment has added step S101 replacing step S16, and has added steps S102 through S104 Between step S101 and step S17 compared to the processing performed by the measuring unit 10a of the first embodiment. The processing performed by the information processing unit 10b of the second embodiment has added step S201 replacing step S22, and has added steps S202 and S203 between steps S23 and step S24 compared to the processing performed by the information processing unit 10b of the first embodiment. The steps which are different from the steps of the first embodiment are described below.

In step S101, the measurement controller 11 determines whether a first predetermined time has elapsed since step S14 first started. The measurement controller 11 repeats steps S14 and S15 until the first time has elapsed. In this way, when the measurement sample flowing through the flow cell 110 during the first time is designated a first part, the information related to the blood cells is obtained based on this first part. The information related to blood cells based on the first part is used to classify red blood cells and platelets. The measurement controller 11 continues the process of flowing the measurement sample through the flow cell 110, and the process of irradiating the first light 210 and the second light 220 on the measurement sample and receiving each produced light.

In step S102, the measurement controller 11 determines whether the first scattered light information is greater than the threshold value V2 shown in FIG. 10A. When the determination is YES in step S102, the measurement controller 11 mutually associates the first scattered light information, second scattered light information, third scattered light information, and fluorescent light information produced from the same blood cell, and stores the associated information in the memory unit 11a in step S103. In this way the blood cells for which the first scattered light information is below the threshold value V2 are excluded from analysis.

In step S104, the measurement controller 11 determines whether a second predetermined time has elapsed since step S102 first started. The second time is longer than the first time. The measurement controller 11 repeats steps S102 and S103 until the second time has elapsed. In this way, when the measurement sample flowing through the flow cell 110 during the second time is designated a second part, the information related to the blood cells is obtained based on this second part. The information related to blood cells based on the second part is used to classify white blood cells.

The white blood cells in the measurement sample are several stages smaller than red blood cells. However, the amount of the second part is greater than the amount of the first part since the speed of the measurement sample flowing through the flow cell 110 is constant and the second time is longer than the first time. In steps S102 through S104, accuracy of the classification and count of the white blood cells therefore is higher because sufficient information related to white blood cells is obtained. As shown in scattergram 700 of FIG. 10A, the storage capacity of the memory unit 11a is efficiently used because most information related to red blood cells is not stored in the memory unit 11a.

Also, two measurement samples which have different concentrations may be prepared in the sample preparing unit 13, then information related to red blood cells and information related to platelets may be obtained using the low concentration measurement sample, and information related to white blood cells may be obtained using the high concentration measurement sample In this case sufficient information related to white blood cells also can be obtained.

In step S201, the processing unit 21 counts the number of blood cells in regions 410 and 430 based on the scattergram 400 shown in FIG. 6A, and obtains the red blood cell count and platelet count, respectively. The scattergram 400 in this case is based on the information obtained from the first part of the measurement sample.

In step S202, the processing unit 21 counts the number of blood cells within regions 710, 711, 712, and 713 based on the scattergram 700 shown in FIG. 10A, and obtains the white blood cell count, lymphocyte count, monocyte count, and granulocyte count. The scattergram 700 in this case is based on the information obtained from the second part of the measurement sample. In step S203, the processing unit 21 counts the number of blood cells within region 731 based on the scattergram 730 shown in FIG. 10C, and obtains the eosinophil count.

Thus, the processing unit 21 classifies and counts white blood cells by setting the region 710 based on the first scattered light information and the second scattered light information. The processing unit 21 classifies and counts white blood cells into three subgroups by setting regions 711 through 713 based on the first scattered light information and the second scattered light information. The processing unit 21 classifies and counts eosinophils by setting the region 731 based on the first scattered light information, second scattered light information, and fluorescent light information.

Figure 12:
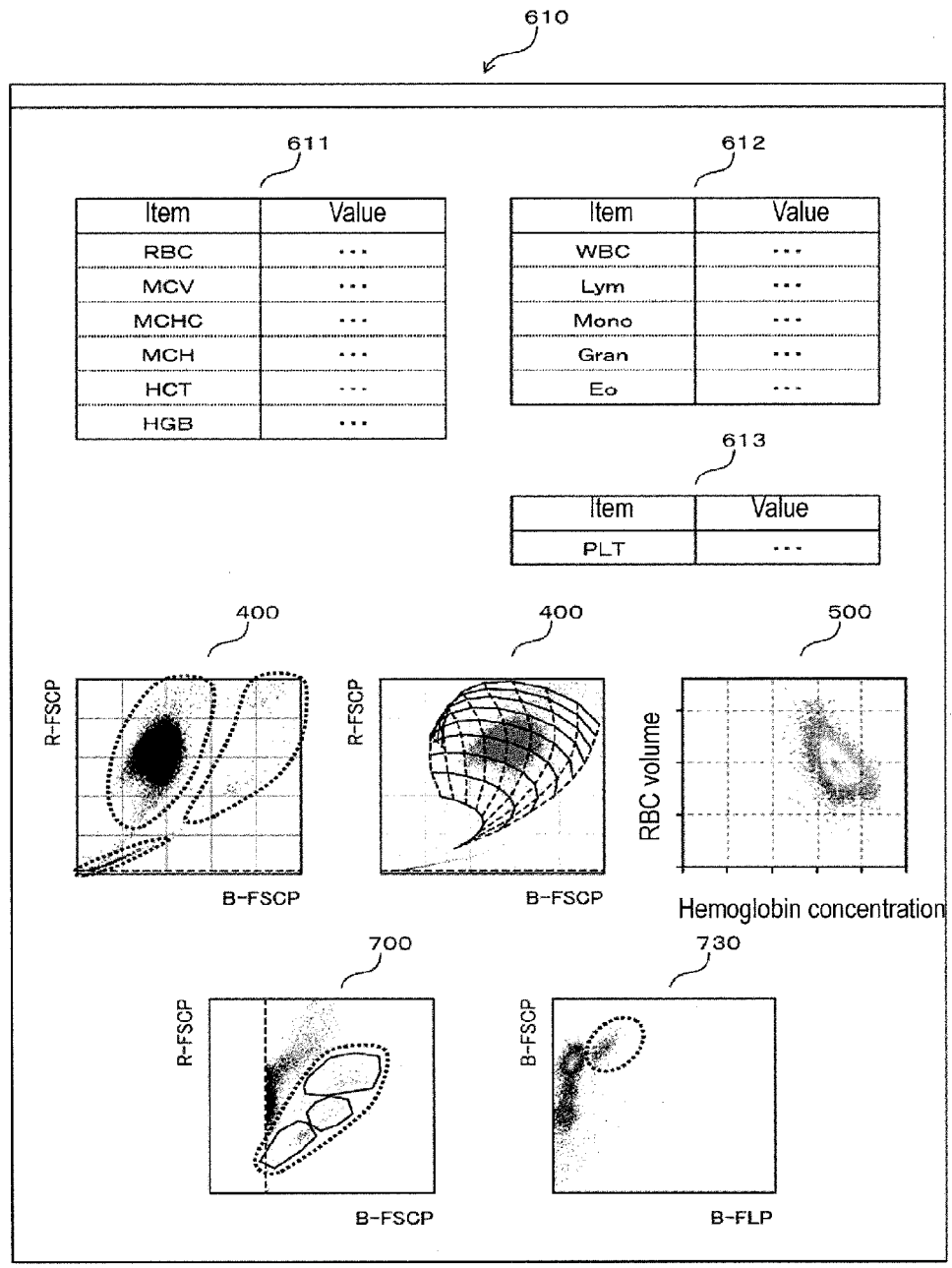
FIG. 12 shows a screen shown on the output unit of the second embodiment.

In step S24, the processing unit 21 displays a screen 610 shown in FIG. 12 on the output unit 22. The screen 610 includes lists 611 through 613, scattergram 400 shown in FIGS. 6A and 6B, scattergram 500 shown in FIG. 6C, scattergram 700 shown in FIG. 10A, and scattergram 730 shown in FIG. 10C. The lists 611 through 613 include values obtained in steps S201 and S23. The list 612 includes values obtained in steps S202 and S203.

Information related to white blood cells and platelets also may be obtained using the second part of the measurement sample. In this case the measurement controller 11 stores the information based on each light in step S102 when the second scattered light information is greater than the threshold value V1. The processing unit 21 classifies and counts the red blood cells based on information obtained from the first part of the measurement sample, and classifies and count white blood cells and platelets based on information obtained from the second part of the measurement sample. Classification and counting accuracy can be increased for white blood cells and platelets which are fewer than red blood cells since the information related to white blood cells and platelets is obtained using the second part which is a larger quantity than the first part.

Figure 13:
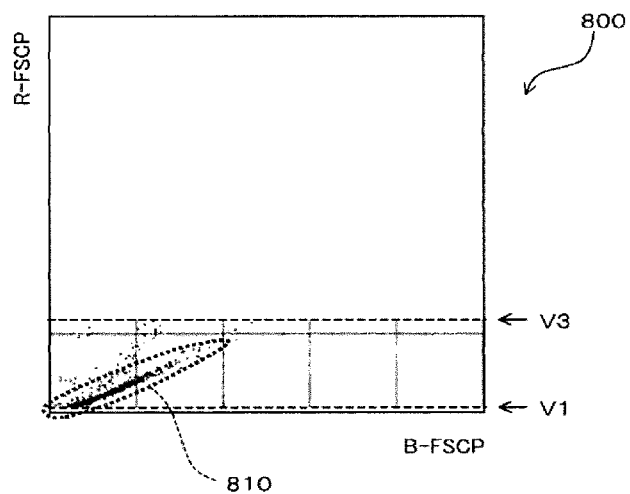
FIG. 13 is a scattergram for classifying platelets of a modification of the second embodiment.

After the first part and the second part of the measurement sample have been measured, a third part of the measurement sample of only a third time also may be measured. In this case the third time is longer than the first time, and the amount of the third part is greater than the amount of the first part. The measurement controller 11 stores the information based on each light in the memory unit 11*a* when the second scattered light information is greater than the threshold value V1 but less than a threshold value V3. The processing unit 21 counts the number of blood cells within region 810 based on the scattergram 800 shown in FIG. 13, and obtains the platelet count. The horizontal axis and the vertical axis of the scattergram 800 are the same as the scattergram 400. The scattergram 800 is based on the information obtained from the third part.

Then, the accuracy of actually obtained lymphocyte count, monocyte count, and granulocyte count are verified.

In this verification the results obtained by processing of the second embodiment, and the results obtained by a reference method of preparing measurement samples using reagents including hemolytic agent and staining agent were compared based on eight blood samples collected from different subjects.

Figure 14A:
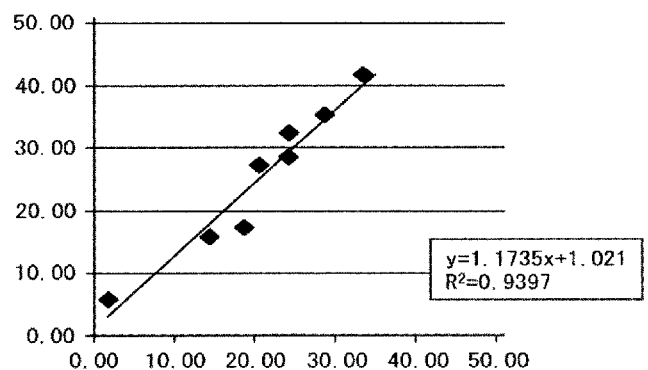
FIG. 14A through 14C show the correlations of results from the second embodiment and results from a reference method.
Figure 14B:
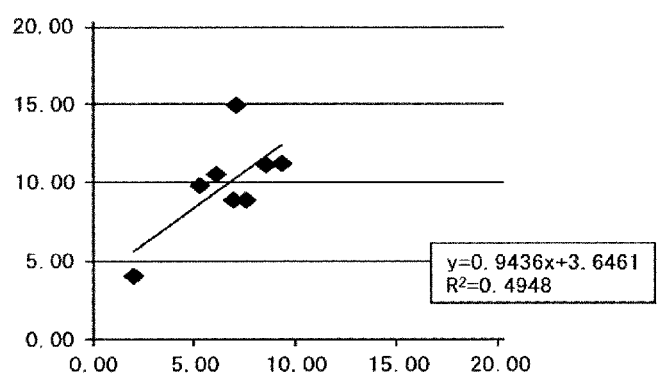
Figure 14C:
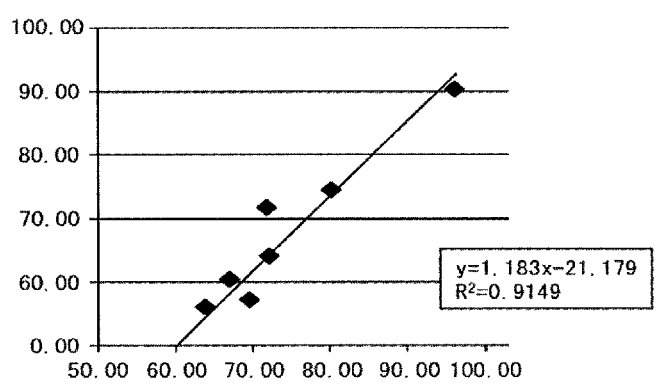

The vertical axis in FIG. 14A through 14C respectively represents the ratio of total blood cells to blood cells obtained by the second embodiment. The horizontal axis in FIG. 14A through 14C respectively represents the ratio of total blood cells to blood cells obtained by the reference method. Values from the second embodiment and values from the reference method were set as parameters, and the points corresponding to the eight blood samples were plotted on the graphs of FIG. 14A through 14C. The graphs of FIG. 14A through 14C show an approximation line of the points corresponding to the eight blood samples. FIG. 14A through 14C show the values of correlation coefficient R and the results from the second embodiment and results from the reference method, and equations of the approximation lines when the horizontal axis is designated x and the vertical axis is designated y. The slope of the approximation line and the value of the correlation coefficient invariably approach [1], and the correlation of the results from the second embodiment and the results from the reference method increases.

As shown in FIGS. 14A and 14C, the correlation of lymphocytes and granulocytes in the results from the second embodiment and results from the reference method is relatively high. It is understood that the results for lymphocytes and granulocytes in the second embodiment have the same degree of accuracy as using the reference method of preparing the measurement samples using reagents such as hemolytic agent and staining agent. On the other hand, there is a slightly lower correlation for monocytes in the results of the second embodiment and results of the reference method, as shown in FIG. 14B. In the second embodiment, however, there is a possibility of increasing the correlation of the results for monocytes by the second embodiment and the results for monocytes by the reference method by adjusting the second time and the degree of dilution of the measurement sample.

What is claimed is:

1. A blood analyzer comprising:
   a sample preparing unit configured to prepare a measurement sample from a blood sample and a reagent without lysing red blood cells in the blood sample;
   a flow cell configured to flow the measurement sample containing blood cells;
   a first light source configured to irradiate light of a first wavelength on the measurement sample flowing through the flow cell;
   a second light source configured to irradiate light of a second wavelength which is different from the first wavelength on the measurement sample flowing through the flow cell;
   a first light receiving part configured to receive a first scattered light obtained by irradiating light from the first light source on the blood cells flowing through the flow cell;
   a second light receiving part configured to receive a second scattered light obtained by irradiating light from the second light source on the blood cells flowing through the flow cell; and
   a processing unit programmed to obtain values related to the number of red blood cells, the number of white blood cells, and hemoglobin based on a first scattered light information based on the signals output from the first light receiving part obtained by measuring the measurement sample, and a second scattered light information based on the signals output from the second light receiving part obtained by measuring the measurement sample.

2. The blood analyzer of claim 1, wherein the processing unit is programmed to obtain the platelet count based on the first scattered light information and the second scattered light information.

3. The blood analyzer of claim 1, wherein the processing unit is programmed to obtain values related to the red blood cell volume based on the first scattered light information which is based on the signals output from the first light receiving part, and the second scattered light information which is based on the signals output from the second light receiving part.

4. The blood analyzer of claim 3, wherein the processing unit is programmed to obtain values related to hemoglobin concentration and values related to red blood cell volume from the first scattered light information and the second scattered light information using conversion information which defines the relationship of the combination of the first scattered light information and the second scattered light information, and the combination of the red blood cell volume and the hemoglobin concentration.

5. The blood analyzer of claim 4, wherein the processing unit is programmed to obtain the mean corpuscular hemoglobin concentration based on the red blood cell count and the value related to hemoglobin concentration.

6. The blood analyzer of claim 3, wherein the processing unit is programmed to obtain the mean corpuscular volume based on the red blood cell count and the value related to the red blood cell volume.

7. The blood analyzer of claim 6, wherein the processing unit is programmed to obtain a hematocrit value based on the red blood cell count and the mean corpuscular volume.

8. The blood analyzer of claim 7, wherein the processing unit is programmed to obtain the amount of hemoglobin based on the hematocrit value and the mean corpuscular hemoglobin concentration.

9. The blood analyzer of claim 1, wherein the processing unit is programmed to classify and count white blood cells into a plurality of subgroups based on the first scattered light information and the second scattered light information.

10. The blood analyzer of claim 1, wherein the red blood cell count is obtained based on the first scattered light information and the second scattered light information obtained by measuring a first part of the measurement sample, and the white blood cell count is obtained based on the first scattered light information and the second scattered light information obtained by measuring a second part which is larger than the first part.

11. The blood analyzer of claim 10, wherein the red blood cell count is obtained based on the first scattered light information and the second scattered light information obtained by measuring the measurement sample flowing through the flow cell at a first time as the first part of the measurement sample, and the white blood cell count is obtained based on the first scattered light information and the second scattered light information obtained by measuring the measurement sample flowing through the flow cell at a second time which is longer than the first time as the second part of the measurement sample.

12. The blood analyzer of claim 10, wherein the blood cells for which the first scattered light information is less than a predetermined threshold value are eliminated from the analysis in the processing of the second part of the measurement sample.

13. The blood analyzer of claim 1, wherein the first light source is configured to irradiate light at a wavelength of 400 nm or greater but no more than 435 nm, and the second light source is configured to irradiate light at a wavelength of 610 nm or greater but no more than 750 nm.

14. The blood analyzer of claim 1, further comprising: an output unit configured to output the value obtained by the processing unit.

15. The blood analyzer of claim 14, wherein the output unit is configured to display scattergrams in which the first scattered light information and the second scattered light information are plotted together with values related to hemoglobin as the coordinate axes.

16. The blood analyzer of claim 14, wherein the output unit is configured to display scattergrams in which the values related to red blood cell volume and values related to hemoglobin concentration, are plotted together with values related to hemoglobin as coordinate axes.

17. A blood analyzing method comprising:
preparing a measurement sample from a blood sample and a reagent without lysing red blood cells in the blood sample;
irradiating a first light having a first wavelength and irradiating a second light having a second wavelength which is different from the first wavelength on a measurement sample containing blood cells;
receiving a first scattered light obtained by irradiating the first light on a blood cell, and receiving a second scattered light obtained by irradiating the second light on the blood cell; and
obtaining values related to the number of red blood cells, the number of white blood cells and hemoglobin based on the first scattered light information which is based on the first scattered light obtained by measuring the measurement sample, and the second scattered light information which is based on the second scattered light obtained by measuring the measurement sample.

18. The blood analyzing method of claim 17, wherein the first wavelength is 400 nm or greater but no more than 435 nm, and the second wavelength is 610 nm or greater but no more than 750 nm.

\* \* \* \* \*